US012051493B2

(12) United States Patent
Ogawa et al.

(10) Patent No.: US 12,051,493 B2
(45) Date of Patent: Jul. 30, 2024

(54) MEDICATION ADMINISTRATION STATUS MANAGEMENT DEVICE, METHOD, AND NON-TRANSITORY RECORDING MEDIUM THAT RECORDS PROGRAM

(71) Applicant: OMRON HEALTHCARE Co., Ltd., Kyoto (JP)

(72) Inventors: Hiroshi Ogawa, Kyoto (JP); Asa Hirasawa, Kyoto (JP); Tamio Ueda, Kyoto (JP); Kensuke Ibata, Kyoto (JP); Tomoya Ishida, Kyoto (JP); Hideyuki Kobayashi, Kyoto (JP); Mizuki Furuta, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 290 days.

(21) Appl. No.: 17/448,134

(22) Filed: Sep. 20, 2021

(65) Prior Publication Data
US 2022/0005571 A1 Jan. 6, 2022

Related U.S. Application Data

(63) Continuation of application No. PCT/JP2020/008797, filed on Mar. 3, 2020.

(30) Foreign Application Priority Data

Mar. 25, 2019 (JP) ................................ 2019-057045

(51) Int. Cl.
| | | |
|---|---|---|
| *G16H 20/10* | (2018.01) | |
| *A61B 5/00* | (2006.01) | |
| *G16H 10/60* | (2018.01) | |

(52) U.S. Cl.
CPC ........... *G16H 20/10* (2018.01); *A61B 5/4833* (2013.01); *G16H 10/60* (2018.01)

(58) Field of Classification Search
CPC ........ G16H 20/10; G16H 10/60; G16H 15/00; G16H 40/67; A61B 5/4833
See application file for complete search history.

(56) References Cited

U.S. PATENT DOCUMENTS

| | | | | |
|---|---|---|---|---|
| 2011/0175735 | A1* | 7/2011 | Forster | A61B 5/002 340/10.4 |
| 2012/0157793 | A1 | 6/2012 | MacDonald | |

(Continued)

FOREIGN PATENT DOCUMENTS

| | | |
|---|---|---|
| CN | 102646157 A | 8/2012 |
| CN | 104966256 A | 10/2015 |

(Continued)

OTHER PUBLICATIONS

International Search Report for International Application No. PCT/JP2020/008797, dated Jun. 2, 2020.

(Continued)

*Primary Examiner* — Meredith A Long
(74) *Attorney, Agent, or Firm* — Birch, Stewart, Kolasch & Birch, LLP

(57) ABSTRACT

To ensure further accurate management of a status of medication administration, one aspect of the present invention acquires declaration information regarding the medication administration of a user, acquires biological information of the user and causes a storage medium to store the biological information, calculates a degree of dispersion of the biological information acquired in a target period based on the biological information stored in the storage medium, determines reliability of the declaration information regarding the medication administration acquired in the target period based on the degree of dispersion of the biological information, and outputs information representing a determination result of the reliability.

13 Claims, 9 Drawing Sheets

(56) References Cited

U.S. PATENT DOCUMENTS

| | | | |
|---|---|---|---|
| 2017/0147775 A1* | 5/2017 | Ohnemus | G16H 50/50 |
| 2017/0246086 A1* | 8/2017 | Jain | A61B 5/4833 |
| 2021/0082558 A1* | 3/2021 | Sato | A61B 5/4839 |

FOREIGN PATENT DOCUMENTS

| | | |
|---|---|---|
| JP | 2002-183306 A | 6/2002 |
| JP | 2018-151993 A | 9/2018 |
| JP | 2018-164601 A | 10/2018 |
| WO | 2018/235652 A1 | 12/2018 |

OTHER PUBLICATIONS

International Preliminary Report on Patentability for International Application No. PCT/JP2020/008797, dated Oct. 2, 2020.
English translation of the International Preliminary Report on Patentability for International Application No. PCT/JP2020/008797, dated Oct. 2, 2020.
Chinese Office Action and Search Report for Chinese Application No. 202080019506.0, dated Mar. 29, 2024, with English translation.

* cited by examiner

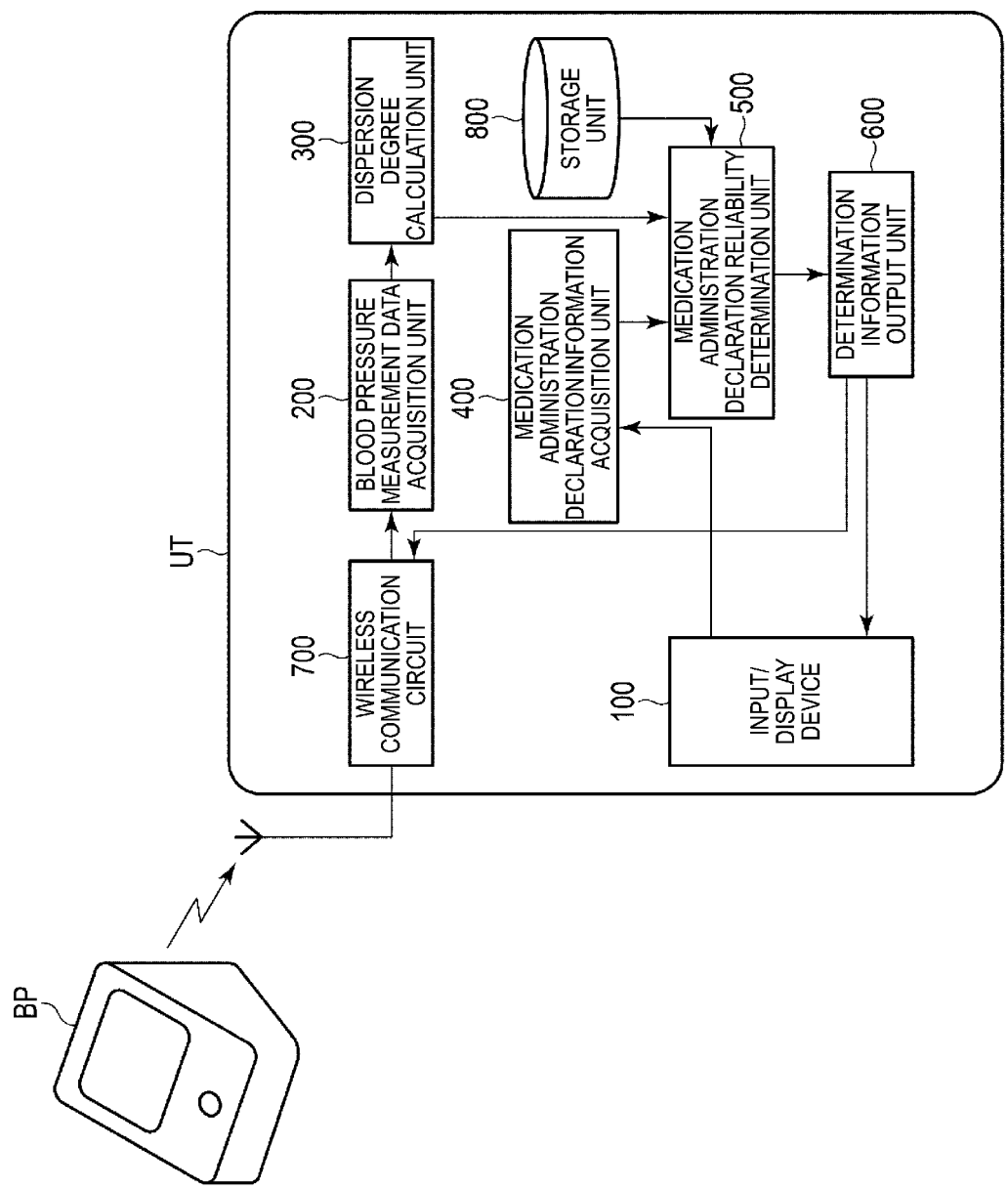
[FIG. 1]

[FIG. 2]
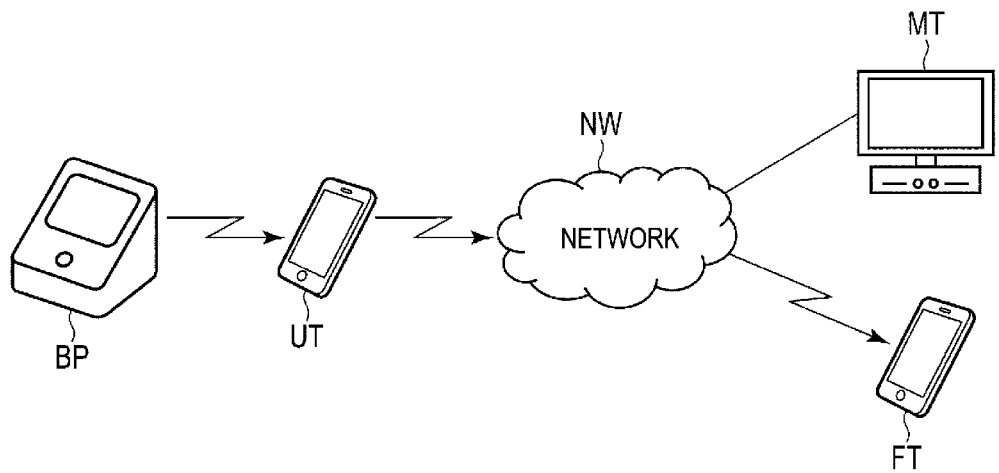
[FIG. 3]
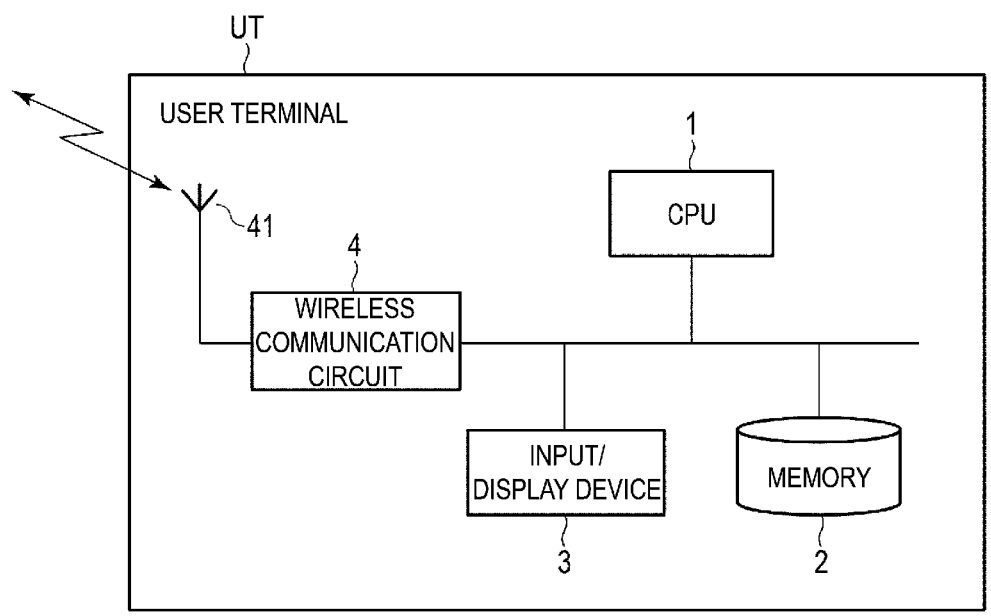

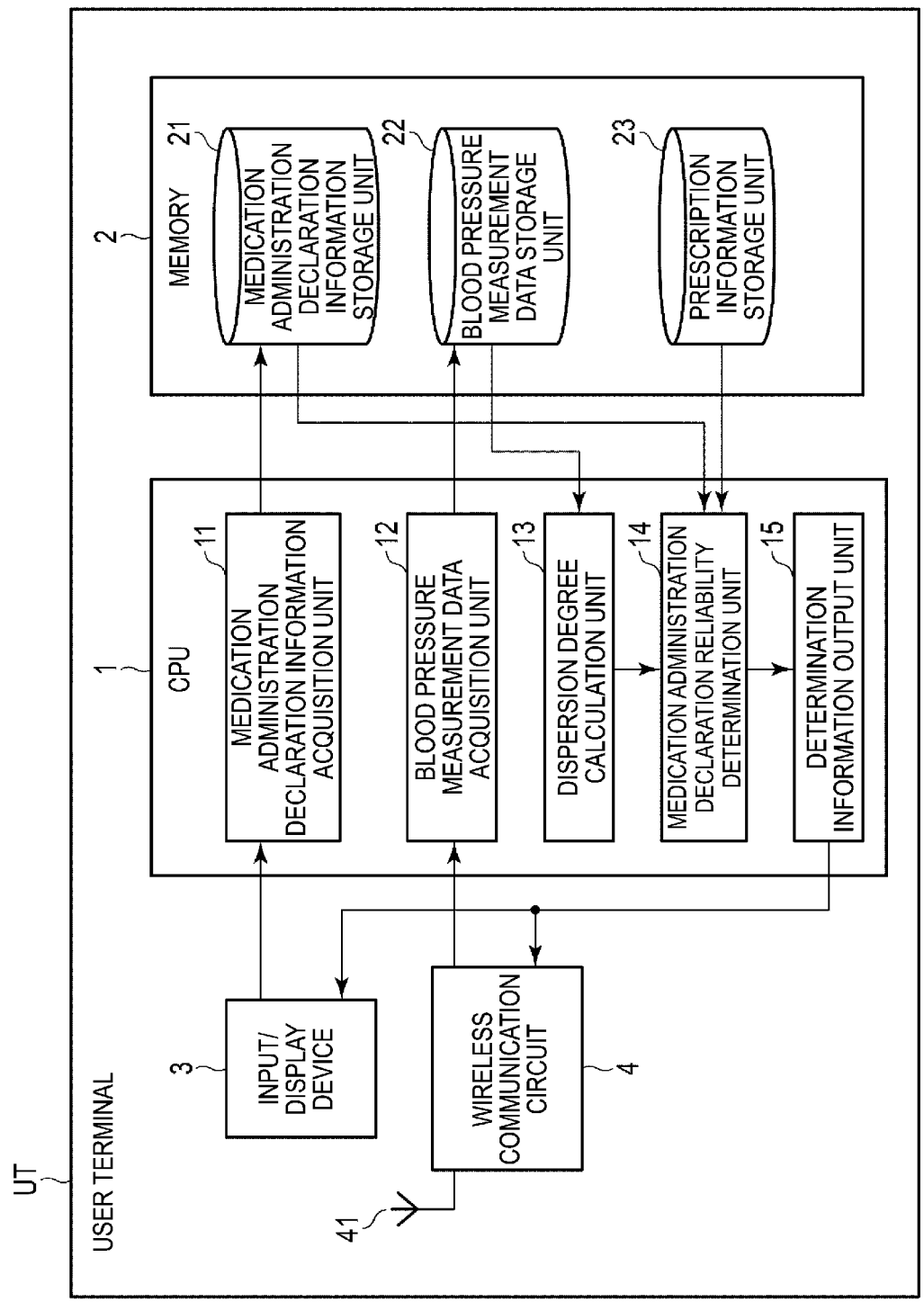
[FIG. 4]

[FIG. 5]
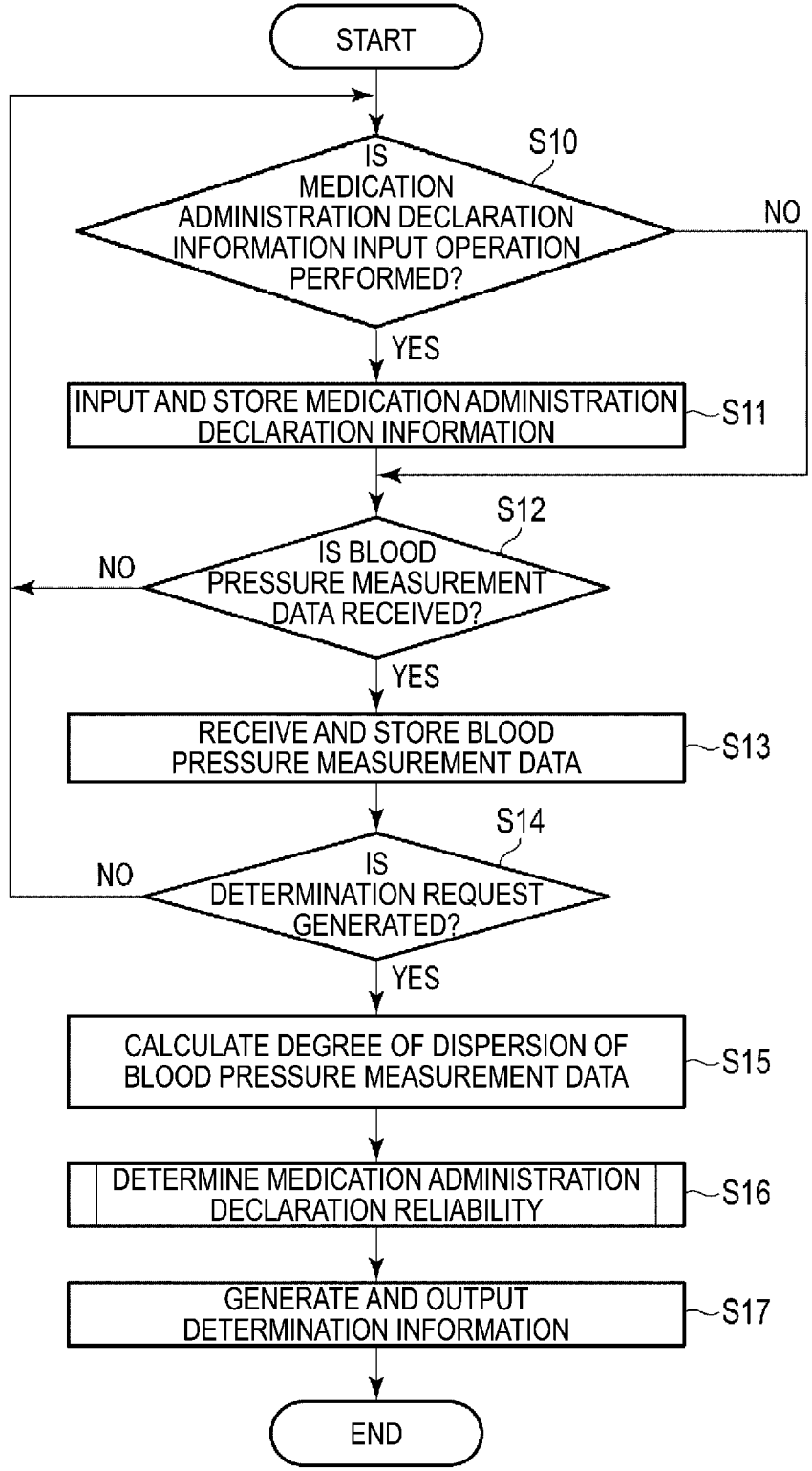

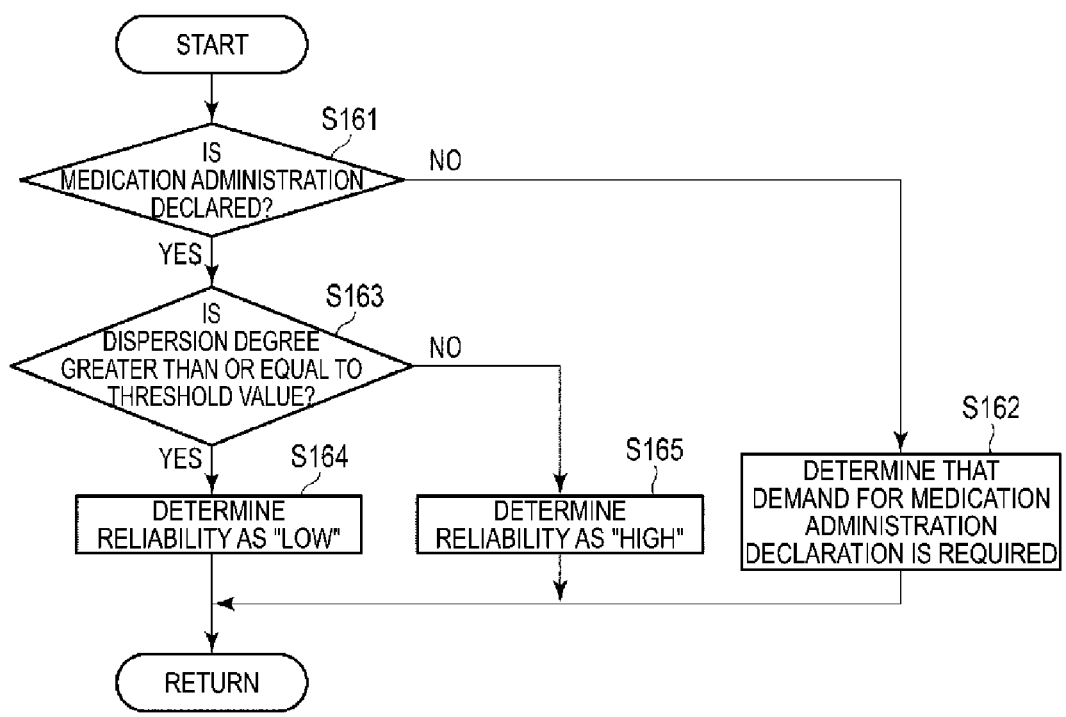
[FIG. 6]

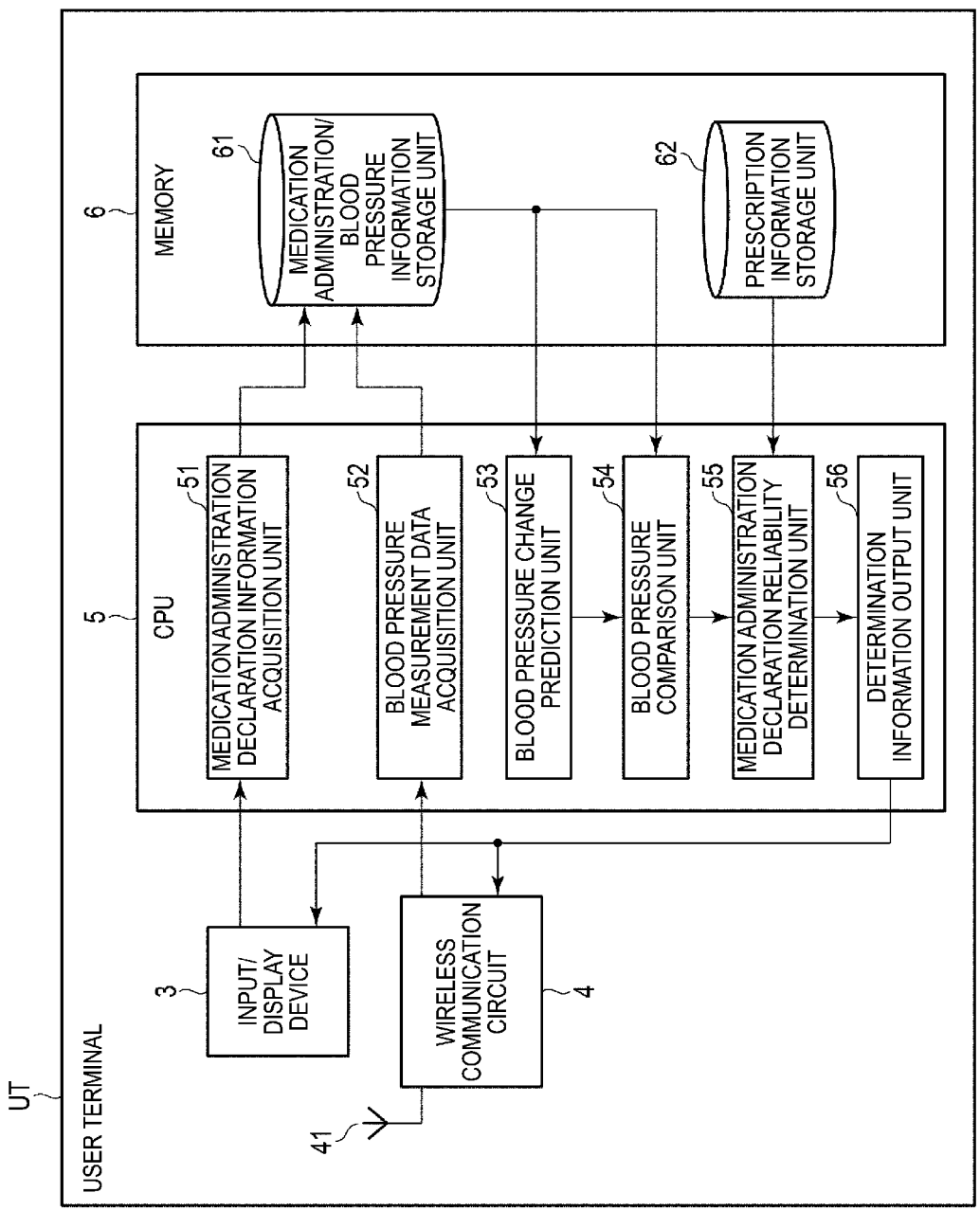
[FIG. 7]

[FIG. 8]
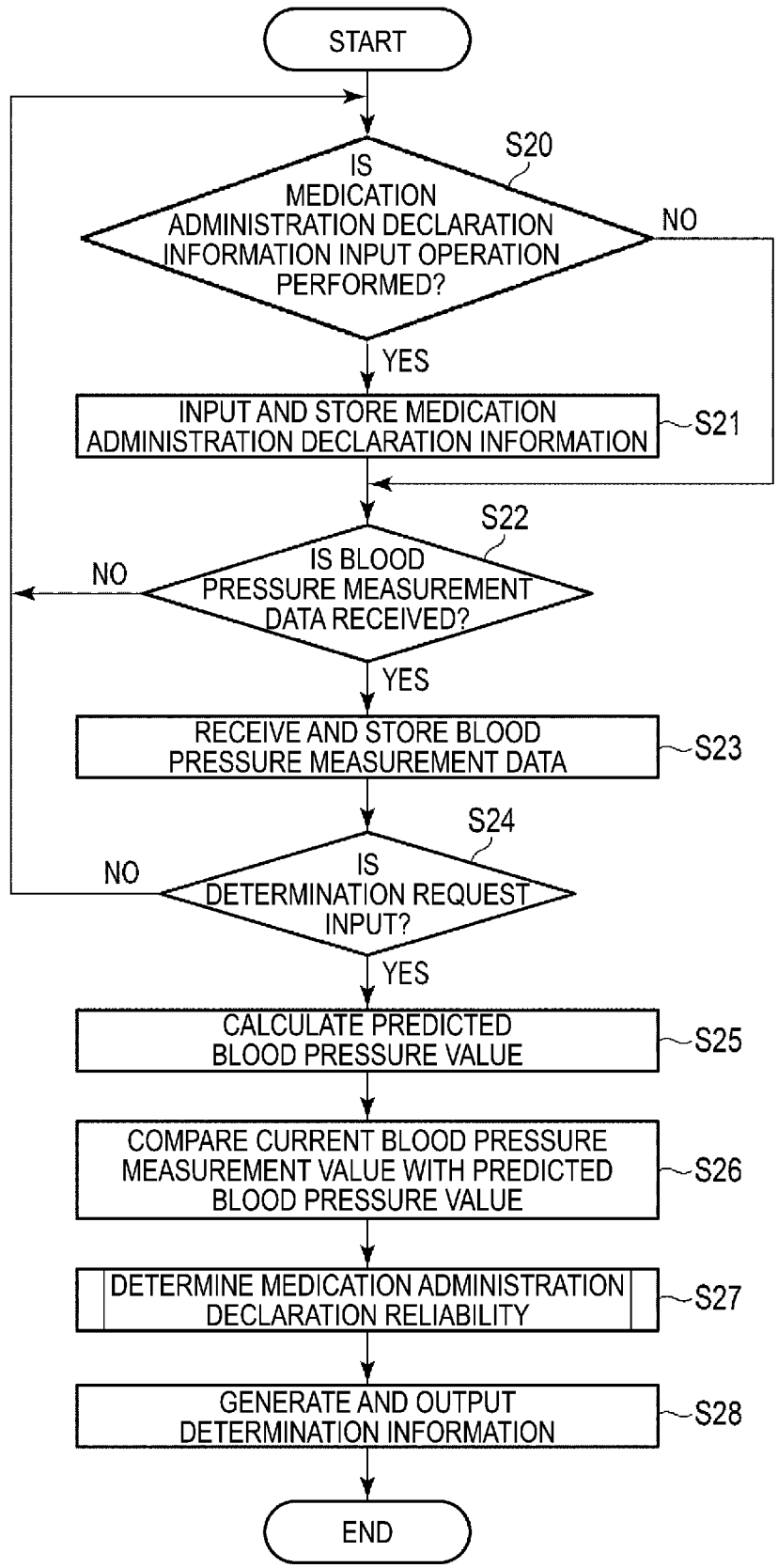

[FIG. 9]
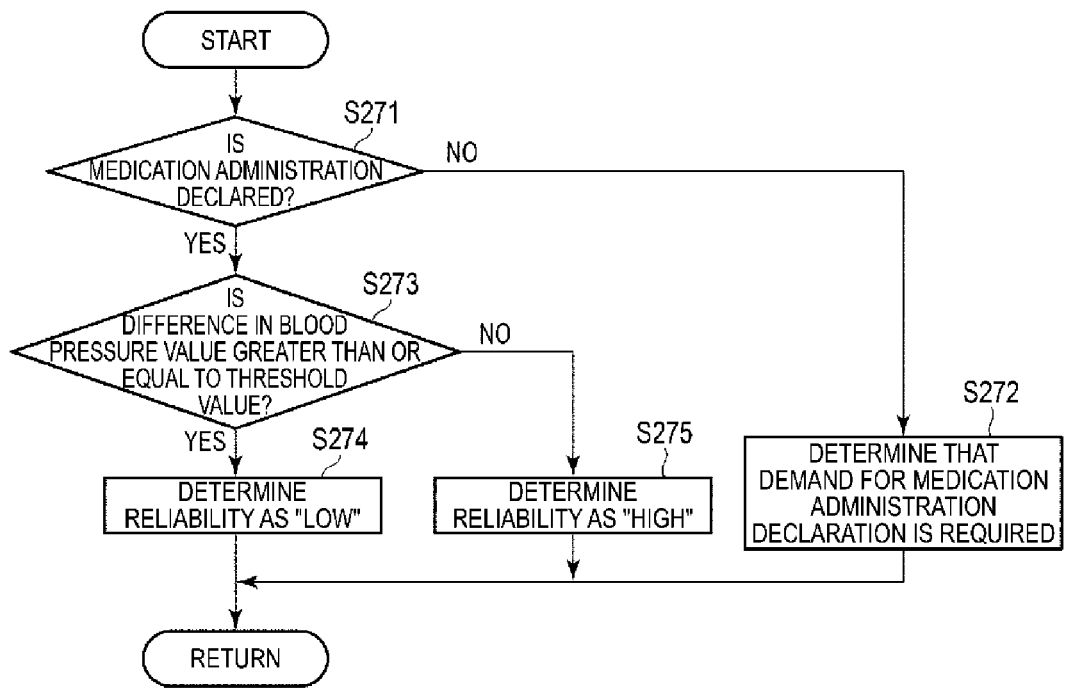

[FIG. 10]

MEDICATION ADMINISTRATION STATUS MANAGEMENT DEVICE, METHOD, AND NON-TRANSITORY RECORDING MEDIUM THAT RECORDS PROGRAM

CROSS-REFERENCE TO RELATED APPLICATIONS

This application is the U.S. national stage application filed pursuant to 35 U.S.C. 365(c) and 120 as a continuation of International Patent Application No. PCT/JP2020/008797, filed Mar. 3, 2020, which application claims priority to Japanese Patent Application No. 2019-057045, filed Mar. 25, 2019, which applications are incorporated herein by reference in their entireties.

TECHNICAL FIELD

Embodiments of the present invention relate to a medication administration status management device, a method, and a non-transitory recording medium that records a program used to manage, for example, a status of medication administration by a user.

BACKGROUND ART

Treatment with medication is one method of treating diseases. It is extremely important in the medication treatment to comply with administration of a medication prescribed by a physician to obtain an intended therapeutic effect.

Thus, for example, there has been proposed the following technology. A patient inputs declaration information representing a medication administration status, such as whether medication administration has been performed, using a mobile information terminal, such as a smartphone. Based on this declaration information, medication administration adherence information representing a status of compliance with the medication administration is generated. This information can be displayed on a terminal of the patient or a terminal of a physician or a pharmacist (for example, see Patent Document 1).

The use of this technology allows a medication administrator, such as a physician and a pharmacist, to accurately grasp a relationship between the medication administration of the patient and the therapeutic effect and therefore is significantly effective. Another is effect is that the patient becomes motivated to continue taking their medication.

CITATION LIST

Patent Literature

Patent Document 1: JP 2018-151993 A

SUMMARY OF INVENTION

Technical Problem

On the other hand, among patients who undergo a medication administration treatment while spending daily life at home, although not administering a medication as described in a prescription, some patients make a false declaration that the medication was administered due to a reason, such as low interest in complying with the medication administration and general busyness. In such circumstances, the above-described prior art does not examine, for example, whether the medication is truly administered for the medication administration declaration by the patient, and therefore a medication administrator, such as a physician and a pharmacist, possibly cannot correctly determine the relationship between the medication administration and the therapeutic effect. This possibly leads to an erroneous medication judgment, such as an increase in dosage and a change of a medicine type, which is considerably undesirable.

The present invention has been made focusing on the circumstances, and attempts to provide a technology that provides information with which a status of medication administration can be more accurately managed.

Solution to Problem

To solve the above problems, one aspect of a medication administration status management device or a method according to the present invention acquires declaration information regarding medication administration of a user, acquires biological information of the user and causes a storage medium to store the biological information, calculates a degree of dispersion of the biological information acquired in a target period based on the biological information stored in the storage medium, determines reliability of the declaration information regarding the medication administration acquired in the target period based on the degree of dispersion of the biological information, and outputs information representing a determination result of the reliability.

Advantageous Effects of Invention

According to an aspect of the present invention, the following effects are provided. That is, in general, the degree of dispersion of the biological information is associated with a compliance status of the medication administration. For example, observing the degree of dispersion of blood pressure values regularly measured every day in the target period for one week, the degrees of dispersion of blood pressure values of patients who comply with the medication administration tend to be small, and conversely, the degrees of dispersion of blood pressure values of patients who do not comply with the medication administration tend to be large. Thus, as in the first aspect according to the present invention, calculating the degree of dispersion of measured values of the biological information, such as a blood pressure, in the target period, determining the reliability of medication administration declaration based on this degree of dispersion, and output it allow, for example, a physician or a pharmacist to accurately infer a status of the medication administration of the user as a patient, and to diagnose an effect brought by the medication.

That is, according to one aspect of the present invention, a technology that provides information with which the status of the medication administration can be more accurately managed can be provided.

BRIEF DESCRIPTION OF DRAWINGS

FIG. 1 is a functional block diagram illustrating one application example of a medication administration status management device according to the present invention.

FIG. 2 is a diagram illustrating an overall configuration of a system including a mobile information terminal as a first embodiment of the medication administration status management device according to the present invention.

FIG. 3 is a diagram illustrating an example of a hardware configuration of the mobile information terminal illustrated in FIG. 2.

FIG. 4 is a diagram illustrating an example of a software configuration of the mobile information terminal illustrated in FIG. 2.

FIG. 5 is a flowchart depicting a procedure and a process content of a medication administration status management process by the mobile information terminal illustrated in FIG. 4.

FIG. 6 is a flowchart depicting an example of a procedure and a process content of a medication administration declaration reliability determination process in the flowchart depicted in FIG. 5.

FIG. 7 is a diagram illustrating an example of a software configuration of a mobile information terminal as a second embodiment of a medication administration status management device according to the present invention.

FIG. 8 is a flowchart depicting a procedure and a process content of a medication administration status management process by the mobile information terminal illustrated in FIG. 7.

FIG. 9 is a flowchart depicting an example of a procedure and a process content of a medication administration declaration reliability determination process in the flowchart depicted in FIG. 8.

FIG. 10 is a diagram illustrating an example of an input template displayed on a user terminal when a declaration for medication administration is input.

DESCRIPTION OF EMBODIMENTS

Embodiments according to one aspect of the present invention will be described below based on the drawings. However, the embodiments described below are merely illustrative of the present invention in all respects.

Application Example

First, one application example of a medication administration status management device according to the present invention will be described. FIG. 1 is a diagram for describing this one application example, a user terminal is denoted as UT and a blood pressure monitor is denoted as BP.

Configuration Example (1) Blood Pressure Monitor

The blood pressure monitor BP is a stationary or an upper arm-attached blood pressure monitor that measures a blood pressure, for example, by oscillometric method, and has a function of transmitting measurement data of the blood pressure to the user terminal UT using a wireless communication circuit employing a short-range wireless data communication standard, such as Bluetooth (registered trademark). Note that a wrist type or a wristwatch blood pressure monitor may be used as the blood pressure monitor, in addition to the stationary or upper arm-attached blood pressure monitor in which a cuff is wound around an upper arm for measurement. Using the wristwatch blood pressure monitor allows automatically measuring a blood pressure intermittently or at a preset time.

(2) User Terminal UT

The user terminal UT is configured of a mobile information terminal, such as a smartphone, possessed by a user as a patient. As functions according to one application example of the present invention, the user terminal UT includes an input/display device 100, a blood pressure measurement data acquisition unit 200, a dispersion degree calculation unit 300, a medication administration declaration information acquisition unit 400, a medication administration declaration reliability determination unit 500, a determination information output unit 600, and a wireless communication circuit 700.

Among these, the blood pressure measurement data acquisition unit 200, the dispersion degree calculation unit 300, the medication administration declaration information acquisition unit 400, the medication administration declaration reliability determination unit 500, and the determination information output unit 600 are achieved, for example, by causing a hardware processor to execute a program.

The input/display device 100 is a tablet device in which a capacitive or pressure sensitive type input detection sheet is disposed on a liquid crystal or an organic EL screen, and outputs medication administration declaration information input by an operation of the user to the medication administration declaration information acquisition unit 400. The medication administration declaration information acquisition unit 400 takes in the medication administration declaration information output from the input/display device 100 and causes a memory in the user terminal UT to store the information.

The wireless communication circuit 700 has multiple wireless interface functions that communicate with respective wide area mobile communication network, wireless local area network (LAN), and Bluetooth (registered trademark). In this example, the wireless communication circuit 700 is used to receive the measurement data of the blood pressure transmitted from the blood pressure monitor BP, and to transmit determination information of reliability of the medication administration declaration information input by the user to a terminal of a medication administrator, such as a physician and a pharmacist.

The blood pressure measurement data acquisition unit 200 takes in the measurement data of the blood pressure received by the wireless communication circuit 700 and causes the memory in the user terminal UT to store it.

The dispersion degree calculation unit 300 reads the measurement data of the blood pressure measured in a preset target period (for example, one day or one week) from the memory, and calculates a degree of dispersion (for example, a degree of variation in measured values or a degree of variation in changes in the measured value).

The medication administration declaration information acquisition unit 400 takes in information declaring the status of the medication administration in the medication administration period input by the user in the input/display device 100 and causes the memory in the user terminal UT to store the information.

The medication administration declaration reliability determination unit 500 determines the reliability of the medication administration declaration information input by the user based on the degree of dispersion of the blood pressure measurement data calculated by the dispersion degree calculation unit 300. This reliability is determined, for example, based on the number of times (timing) of the medication administration in one day and the content designated by prescription information. The prescription information is acquired from, for example, the terminal of the physician or the pharmacist or an EMS server in a hospital and stored in a storage unit 800.

For example, the determination information output unit 600 generates a notification message to report a determination result of the reliability of the medication administration declaration information for the medication administrator, such as the physician and the pharmacist, based on the determination result of the reliability of the medication administration declaration information, and causes the wireless communication circuit 700 to transmit the notification message to the terminal of the physician or the pharmacist. For example, the determination information output unit 600 also has a function of generating a notification message demanding the declaration for the medication administration of the user and displaying it on the input/display device 100. Note that the determination information output unit 600 may have a function of generating a communication message for a family member, for example, when the reliability is lower than a threshold value as a result of the determination of the reliability of the medication administration declaration information and transmitting the communication message from the wireless communication circuit 700.

Actions and Effects

With the configuration described above, in the user terminal UT, the blood pressure measurement data acquisition unit 200 acquires the blood pressure measurement data of the user together with the medication administration declaration information of the user in the medication administration period by the medication administration declaration information acquisition unit 400. Based on the acquired blood pressure measurement data, a blood pressure value of the blood pressure measurement data or the degree of dispersion of the changes in the period on a daily or weekly basis is calculated. Based on the calculated degree of dispersion of the blood pressure values, the medication administration declaration reliability determination unit 500 determines the reliability of the medication administration declaration information of the user in the same period, and the determination information output unit 600 outputs the determination information representing the determination result.

Here, generally, the degree of dispersion of the blood pressure values is associated with a compliance status of the medication administration. For example, observing the degree of dispersion of blood pressure values regularly measured every day in the target period for one week, the degrees of dispersion of blood pressure values of patients who comply with the medication administration tend to be small, and conversely, the degrees of dispersion of blood pressure values of patients who do not comply with the medication administration tend to be large.

Thus, as described above, determining the reliability of the medication administration declaration based on the degree of dispersion of the blood pressure values in the target period and transmitting the result to the terminal of the medication administrator allow the medication administrator, such as the physician and the pharmacist, to accurately infer the status of the medication administration of the user as the patient and to diagnose the effect of the medication.

In addition, in the medication administration status management device according to the present invention, the following application example is conceivable.

For example, a medication administration status management device includes a declaration information acquisition unit, a biological information acquisition unit, a prediction unit, a calculation unit, a reliability determination unit, and an output unit. The declaration information acquisition unit acquires declaration information regarding medication administration of a user and causes a storage medium to store the declaration information. The biological information acquisition unit acquires biological information of the user and causes the storage medium to store the biological information in a state in which the biological information is associable with the declaration information having a corresponding acquisition timing. The prediction unit calculates a predicted value of the biological information in a second period in which the biological information is a monitoring target based on the declaration information and the biological information in a first period in which a medication administration status is known and stored in the storage medium. The calculation unit calculates a degree of divergence of an actually measured value of the biological information acquired during the second period with respect to the calculated predicted value of the biological information. The reliability determination unit determines reliability of the declaration information regarding the medication administration in a third period that affects a change in the biological information in the second period based on the calculated degree of divergence. The third period is prior to the second period. The output unit outputs information representing a determination result of the reliability.

According to the configuration, the following effects are provided. That is, generally, a change in the actually measured value of the biological information of the user who complies with the medication administration with respect to the predicted value is considered as small. Therefore, the degree of divergence between the predicted value of the biological information in the second period (the monitoring period of the biological information), which is predicted from the biological information and the declaration information of the medication administration measured in the first period (a prediction reference period) in which the medication administration status is known, and the actually measured value of the biological information actually measured during the second period tends to be small. In contrast, in a case where the user who does not comply with the medication administration declares for medication administration as if the user complied with the medication administration, it is inferred that the degree of divergence between the predicted value of the biological information and the actually measured value of the biological information actually measured in the second period in which the medical efficacy should appear becomes large.

Thus, as in this application example, based on the biological information and the declaration information of the medication administration obtained in the past first period in which the medication administration status is known, the value of the biological information in the second period as the monitoring period of the biological information is predicted. Based on the degree of divergence of the actually measured value of the biological information actually measured with respect to this predicted value, the reliability of the declaration information of the medication administration in the third period, which is prior to the second period, that affects the change in the biological information in the second period is determined and the result is output. This allows the medication administrator, such as the physician and the pharmacist, to further accurately grasping the status of the medication administration in the medication administration period of the user as the patient.

For example, in the medication administration status management device, the reliability determination unit determines whether a degree of dispersion of the biological information or a degree of divergence of an actually measured value with respect to a predicted value of the biological information calculated by the calculation unit is higher than or lower than a threshold value. When the reliability determination unit determines that the degree of dispersion or the degree of divergence of the biological information is higher than the threshold value, the output unit generates a message prompting the medication administration or correct declaration for the medication administration. The output unit outputs the message to at least one of a terminal of the user and a terminal of a person involved having a prescribed relationship with the user.

According to the configuration, in the case where the degree of dispersion or the degree of divergence of the biological information is determined as higher than the threshold value, the message prompting the correct medication administration or declaration for medication administration is generated and is output to the terminal of the user or the terminal of the person involved, such as a family member, having the prescribed relationship with the user. This allows further reliably enlightening the user so as to perform the correct medication administration or declaration for medication administration.

For example, in the medication administration status management device, the reliability determination unit calculates a medication administration ratio representing a ratio of a number of times that the medication is declared to be administered to a total number of declarations for the medication administration in the declaration target period of the medication administration based on the declaration information regarding the medication administration. The reliability determination unit sets the threshold value such that a lower medication administration ratio causes a higher value according to the calculated medication administration ratio.

According to such a configuration, the threshold value is set such that the threshold value becomes higher as the medication administration ratio lowers. This allows further accurate determination when the user declares "taken" although the user does not actually take the medicine.

For example, in the medication administration status management device, the reliability determination unit determines whether there is a missing declaration regarding the medication administration in the declaration information based on the declaration information regarding the medication administration. When the missing of the declaration is determined as present, the reliability determination unit determines that the declaration regarding the medication administration needs to be prompted to the user.

According to the configuration, when the declaration information input by the user is determined as including a missing, it is determined that the declaration regarding the medication administration needs to be prompted to the user. This allows prompting the user to declare the medication administration without omission before the reliability of the declaration information is determined.

For example, when it is determined that the declaration regarding the medication administration needs to be prompted to the user, the medication administration status management device outputs information prompting the declaration regarding the medication administration to the user. The medication administration status management device determines presence or absence of a response from the user to a presentation of the information prompting the declaration regarding the medication administration. When the response is determined as absent, the medication administration status management device regards that the declaration regarding the medication administration is not made and omits a declaration process of the reliability of the declaration information.

According to the configuration, when the user does not input the declaration for the medication administration in response to the demand for the declaration for medication administration, it is regarded that the declaration regarding the medication administration is not made, and the determination process of the reliability of the declaration information is not performed. This allows reducing a process load on the device in a case where the effective declaration information is not input.

For example, the medication administration status management device further includes a medication administration ratio calculation unit and a correction unit. The medication administration ratio calculation unit calculates a medication administration ratio representing a ratio of a number of times that the medication is declared to be administered to a total number of declarations for the medication administration in a declaration target period of the medication administration based on the declaration information regarding the medication administration. The correction unit that corrects the medication administration ratio based on a determination result of the reliability of the declaration information by the reliability determination unit.

According to the configuration, the medication administration ratio is calculated from the declaration information of the medication administration. Therefore, for example, transmission of this medication administration ratio to the terminal of the medication administrator allows the medication administrator to grasp the medication administration status of the user by the value, the medication administration ratio. Moreover, since the medication administration ratio is corrected based on the reliability of the declaration information, the accurate medication administration ratio where an declaration error and a false declaration by the user have been considered can be recognized.

For example, in the medication administration status management device, the output unit transmits the information representing the determination result of the reliability to a terminal used by a medication administrator for the user.

According to the configuration, for example, the medication administrator, such as the physician and the pharmacist, can automatically acquire the reliability of the declaration information of the medication administration of the user, and this can be useful for, for example, examination of a necessity to change the prescription.

For example, in the medication administration status management device, the reliability determination unit causes the storage medium to store the obtained determination result of the reliability. The reliability determination unit updates the determination result of the reliability stored in the storage medium each time a new reliability determination result is obtained.

According to the configuration, the reliability of the medication administration declaration determined in the determination target period of the medication administration declaration reliability is tentatively continued until the reliability of the next medication administration declaration is determined, that is, held for a period after the determination target period to the present.

First Embodiment

Configuration Example (1) System

FIG. 2 is a diagram illustrating an overall configuration of the system including a medication administration status management device according to the first embodiment of the present invention, the user terminal as the medication administration status management device is denoted as UT and the blood pressure monitor as a biological information measurement device is denoted as BP.

The blood pressure monitor BP is a blood pressure monitor, for example, of a type in which a cuff is wound around an upper arm of the user to measure a blood pressure value by oscillometric method, and has a function of transmitting the measurement data of the blood pressure to the user terminal UT over a short-range wireless network, such as Bluetooth (registered trademark). A wrist type or a wristwatch blood pressure monitor may be used as the blood pressure monitor BP, in addition to the type in which the cuff is wound around the upper arm for measurement. Among these, the wristwatch blood pressure monitor can employ, as a measurement method, an oscillometric method or a pulse transit time (PTT), and automatically measure a blood pressure intermittently or at a preset time. Note that, the blood pressure monitor BP can be connected to the user terminal UT via, for example, any wireless network including a wireless Local Area Network (LAN) and a signal cable.

The user terminal UT can transmit data over a network NW between a medication-administrator terminal MT used by the medication administrator, such as the physician and the pharmacist, and a family terminal FT used by the family member of the user. The network NW is formed of, for example, a wide area network that uses the Internet as a core, and an access network for connecting the terminals to this wide area network.

(2) User Terminal UT
(2-1) Hardware Configuration

FIG. 3 is a block diagram illustrating an example of the hardware configuration of the user terminal UT.

The user terminal UT is formed of a mobile information terminal, such as a smartphone or a tablet terminal, possessed by, for example, the user as the patient. The user terminal UT includes a hardware processor 1 (hereinafter also simply referred to as a CPU), such as a Central Process Unit (CPU), and a memory 2, an input/display device 3, and a wireless communication circuit 4 are connected to the CPU 1 via a bus.

For example, the memory 2 uses a combination of a non-volatile memory, such as a Solid State Drive (SSD), that can write and read at any time and a volatile memory, such as a Random Access Memory (RAM), as a storage medium, and includes a program storage area and a data storage area in the storage area. The program storage area is used to store a middleware program that functions as an Operation System (OS) and various application programs. The data storage area is used to store various kinds of data used to determine the reliability of the medication administration declaration information.

The input/display device 3 is configured of, for example, a tablet device in which a capacitive or pressure sensitive input sheet is disposed on a display using a liquid crystal or an organic EL and is used to input operation information by the user and display the display information.

The wireless communication circuit 4 has multiple wireless interface functions that wirelessly communicate with each of a short-range wireless network, such as Bluetooth (registered trademark), a local wireless network within a home or within an enterprise, such as a wireless LAN, and a public mobile communication network provided by a carrier. Among them, the wireless communication circuit 4 receives the measurement data of the blood pressure from the blood pressure monitor BP over the short-range wireless network and performs data transmission with the medication-administrator terminal MT over the local wireless network or the public mobile communication network. Note that a control of, for example, a wireless communication protocol is usually performed in the CPU 1, but may be performed in the wireless communication circuit 4. Note that 41 denotes an antenna.

(2-2) Software Configuration

FIG. 4 is a block diagram illustrating a software configuration of the user terminal UT in association with the hardware configuration illustrated in FIG. 3.

The data storage area in the memory 2 is provided with a medication administration declaration information storage unit 21, a blood pressure measurement data storage unit 22, and a prescription information storage unit 23. The medication administration declaration information storage unit 21 stores input template data used when the user inputs the declaration information of the medication administration. The medication administration declaration information storage unit 21 stores the declaration information of the medication administration input with the input/display device 3 by the user in accordance with the input template data associated with information representing date and time of the medication administration. The blood pressure measurement data storage unit 22 stores the measurement data of the blood pressure transmitted from the blood pressure monitor BP associated with information representing date and time of the measurement. The prescription information storage unit 23 stores the prescription information of the user downloaded from the terminal MT of the medication administrator, such as the physician and the pharmacist, or an Electronic Medical Records (EMR) server.

The CPU 1 includes a medication administration declaration information acquisition unit 11, a blood pressure measurement data acquisition unit 12, a dispersion degree calculation unit 13, a medication administration declaration reliability determination unit 14, and a determination information output unit 15 as process function units according to the first embodiment. These control units 11 to 15 are all achieved by causing the CPU 1 to execute an application program stored in the program memory area in the memory 2.

The medication administration declaration information acquisition unit 11 is activated by, for example, an input request operation of the medication administration declaration by the user, reads the input template data from the medication administration declaration information storage unit 21, and causes the input/display device 3 to display the input template data. Then, the medication administration declaration information acquisition unit 11 performs a process that receives the declaration information of the medication administration input by the user in accordance with a guidance of the input template data from the input/display device 3, associates the declaration information with the information representing the date and time of the medication administration, and causes the medication administration declaration information storage unit 21 to store the declaration information. Note that the medication administration declaration information acquisition unit 11 may, for example, be activated in response to a response operation by the user to the message (a reminder) prompting the declaration for the medication administration.

The blood pressure measurement data acquisition unit 12 is activated by a data transmission request from the blood pressure monitor BP, and performs a process that associates the blood pressure measurement data transmitted from the blood pressure monitor BP and received by the wireless communication circuit 4 with the information representing the date and time of the measurement and causes the blood pressure measurement data storage unit 22 to store the blood pressure measurement data.

The dispersion degree calculation unit 13 reads, from the blood pressure measurement data storage unit 22, the measurement data of the blood pressure including the date and time of the measurement in the determination target period each time the preset determination target period (for example, on a daily or weekly basis) passes. The dispersion degree calculation unit 13 performs a process that calculates the degree of dispersion of the read blood pressure measurement data, for example, the degree of variation of the blood pressure measurement values or the changes.

The medication administration declaration reliability determination unit 14 performs a process that determines the reliability of the medication administration declaration information in the same period input by the user based on the calculation result of the degree of dispersion of the blood pressure measurement data obtained by the dispersion degree calculation unit 13. An example of the reliability determination will be described later.

The determination information output unit 15 performs a process that generates notification information for notifying the medication administrator, the family member of the user, or the user himself/herself of the determination result of the reliability of the medication administration declaration information by the medication administration declaration reliability determination unit 14, and transmits the notification information to the medication-administrator terminal MT or the terminal FT of the family member, or causes the input/display device 3 to display the notification information.

Operation Example

Next, operations of the user terminal UT configured as described above will be described. FIG. 5 and FIG. 6 are flowcharts exemplifying the operations.

(1) Acquisition of Medication Administration Declaration Information

The user terminal UT monitors the operation of the input request for the medication administration declaration information in a standby state in step S10. In this state, assume that the user performed a tap operation on an icon to which, for example, a medication administration declaration function is assigned in the input/display device 3. Then, the user terminal UT activates the medication administration declaration information acquisition unit 11, and first reads the input template data from the medication administration declaration information storage unit 21 and causes the input/display device 3 to display the input template data in step S11.

In this state, for example, when the user inputs the presence or absence of the medication administration after breakfast, after lunch, and after dinner on the day in accordance with the input template, the input information representing the presence or absence of the medication administration at each meal is received from the input/display device 3 and the medication administration declaration information storage unit 21 is caused to store the information. At this time, information representing date and time of the declaration is given to each piece of the information representing the presence or absence of the medication administration.

For example, some users possibly input the declaration for the medication administration for one day at once after dinner, before going to bed, or the next day or later. In such a case, in a case where the date and time of the input is directly regarded as the date and time of the medication administration, the date and time of the declared medication administration differs from the true date and time of the medication administration.

Therefore, for example, as illustrated in FIG. 10, the input template includes checkboxes 31a, 32a, and 33a for inputting the presence or absence of the medication administration, and input fields 31b, 32b, and 33b for the time of the medication administration corresponding to each of after breakfast, after lunch, and after dinner described above about a date and time 30 that is not input. Then, the medication administration declaration information storage unit 21 is caused to store the information representing the presence or absence of the medication administration and the information representing the medication administration time input to the corresponding checkboxes 31a, 32a, and 33a and input fields 31b, 32b, and 33b for each of the breakfast, the lunch, and the dinner as the medication administration declaration information. Note that the input template illustrated in FIG. 10 as an example displays a medicine type 34 target for the medication administration. By displaying the medicine type, for example, the user who administers multiple types of medicines can input the medication administration declaration information without a mistake for each medicine type.

After that, each time the user performs the input request operation of the medication administration declaration, under the control by the medication administration declaration information acquisition unit 11, the user terminal UT performs a process that receives the above-described medication administration declaration information and causes the medication administration declaration information storage unit 21 to store it.

(2) Acquisition of Blood Pressure Measurement Data

In the standby state, the user terminal UT monitors the transmission request for the blood pressure measurement data from the blood pressure monitor BP in step S12. In this state, when receiving the transmission request for the blood pressure measurement data from the blood pressure monitor BP, the user terminal UT activates the blood pressure measurement data acquisition unit 12, takes in the blood pressure measurement data transmitted from the blood pressure monitor BP and received by the wireless communication circuit 4 from the wireless communication circuit 4, and causes the blood pressure measurement data storage unit 22 to store the measurement blood pressure data in step S13. At this time, since the information representing the date and time of the measurement is transmitted along with the blood pressure measurement data, the user terminal UT associates the blood pressure measurement data with the date and time of the measurement and causes the blood pressure measurement data storage unit 22 to store the data.

Thereafter, each time the user terminal UT receives the transmission request from the blood pressure monitor BP, the user terminal UT performs reception and storage processes of the above-described blood pressure measurement data under the control by the blood pressure measurement data acquisition unit 12.

(3) Calculation of Degree of Dispersion of Blood Pressure Measurement Data

The user terminal UT monitors a determination request for medication administration declaration reliability while performing the acquisition process of the medication administration declaration information and the acquisition process of the blood pressure measurement data in step S14. In this state, when the determination request is generated from a soft timer in the CPU 1, for example, at the end of the determination target period, for example, one day or one week, the user terminal UT activates the dispersion degree calculation unit 13. Then, under the control by the dispersion degree calculation unit 13, in step S15, the blood pressure measurement data including the date and time of the measurement in the most recent determination target period is read from the blood pressure measurement data storage unit 22 and the degree of dispersion of the blood pressure measurement data is calculated based on each piece of the read blood pressure measurement data.

The degree of dispersion can be obtained, for example, as a standard deviation or a dispersion of all compression period blood pressure values measured in the determination target period, a difference between the highest value and the lowest value among all of the compression period blood pressure values, the number of or a proportion of compression period blood pressure values exceeding an allowable blood pressure variation range that is set with the average value of all of the compression period blood pressure values as the center.

Note that in the above example, the case in which the determination request occurs at the end of the determination target period has been described. However, no such limitation is intended. For example, the determination request may be transmitted from the terminal MT of the medication administrator, such as the physician or the pharmacist, or the terminal FT of the family member, and at the time point of receiving the determination request, the degree of dispersion of the blood pressure measurement values in a certain period before this time point (for example, one day or one week) may be calculated.

(4) Determination of Medication Administration Declaration Reliability

When the degree of dispersion of the blood pressure measurement data is calculated, the user terminal UT then activates the medication administration declaration reliability determination unit 14. Then, under the control by the medication administration declaration reliability determination unit 14, the reliability of the medication administration declaration information corresponding to the determination target period stored in the medication administration declaration information storage unit 21 is determined in step S16.

FIG. 6 is a flowchart depicting an example of a process procedure and a process content of the determination process of the medication administration declaration reliability. The medication administration declaration reliability determination unit 14 first reads the medication administration declaration information corresponding to the determination target period from the medication administration declaration information storage unit 21 and determines whether any medication administration declaration has been made based on the medication administration declaration information in step S161. In other words, the presence or absence of a missing in the medication administration declaration is determined.

For example, in a case where the determination target period is one day, insofar as the number of times that the medication administration declaration is not made is at least one time among the number of medication administrations designated in the prescription information stored in the prescription information storage unit 23, the medication administration declaration is determined as absent in the day. For example, in a case where the determination target period is one week, when the number of days in which the medication administration declaration is not made at all is one day or more or the prescribed number of days or more, it is determined that the medication administration declaration is absent in this week. In the case where the medication administration declaration is determined as absent, the medication administration declaration reliability determination unit 14 regards that the medication administration declaration information is out of the determination target of the medication administration declaration reliability, determines that "a demand to the user for the medication administration declaration is required," and passes the determination result to the determination information output unit 15 in step S162.

On the other hand, when the medication administration declaration is determined as present in the step S161, the medication administration declaration reliability determination unit 14 next determines whether the degree of dispersion of the blood pressure measurement data calculated by the dispersion degree calculation unit 13 is greater than or equal to a threshold value in step S163. As a result of the determination, in the case of the degree of dispersion being greater than or equal to the threshold value, the medication administration declaration reliability determination unit 14 determines that the reliability of the medication administration declaration information in the determination target period is "low" in step S164. In contrast, in the case of the degree of dispersion being less than the threshold value, the medication administration declaration reliability determination unit 14 determines that the reliability of the medication administration declaration information in the determination target period is "high" in step S165.

Note that the information of the medication administration declaration includes information representing the presence or absence of the declaration, that is, both of the declaration of "taken" and the declaration of "not taken." Therefore, the medication administration declaration reliability determination unit 14 calculates the medication administration ratio (the number of declarations of "taken"/ the total number of declarations of medication administration (the number of declarations of "taken"+the number of declarations of "not taken")) and sets a determination threshold value of the degree of dispersion for each calculated medication administration ratio. That is, the determination threshold value is set such that the threshold value becomes high as the medication administration ratio lowers. In this way, more accurate determination can be made.

That is, in a case where the medicine is not actually administered, the degree of dispersion of blood pressure values increases. However, with the threshold value not adjusted, in a case where the correct declaration "not taken" is made, since the dispersion is large, the reliability is determined as "low" despite that the correct declaration is made. However, adjusting the threshold value as described above allows avoiding the erroneous determination.

(5) Output of Determination Result of Medication Administration Declaration Reliability When the medication administration declaration reliability determination unit 14 terminates the determination of the medication administration declaration reliability, the user terminal UT activates the determination information output unit 15. Then, under the control by the determination information output unit 15, based on the determination result received from the medication administration declaration reliability determination unit 14, a notification message to notify the user himself/herself, the medication administrator, such as the physician and the pharmacist, or the family member of this determination result is generated in step S17. Then, the notification message for the user himself/herself is output to the input/display device 3 to be displayed, and the notification message for the medication administrator or the family member is output to the wireless communication circuit 4 and transmitted from the wireless communication circuit 4 to the terminal MT of the medication administrator or the terminal FT of the family member. Note that in this case, the notification message for the user may include a "message that demands the medication administration itself" together with a "message that prompts the correct declaration for medication administration."

Note that, in this example, the case in which only the determination information of the reliability of the medication administration declaration is transmitted to the terminal MT of the medication administrator or the terminal FT of the family member has been described. This assumes the case that the medication administration declaration information of the user has been transmitted to the terminal MT of the medication administrator or the terminal FT of the family member by another process. In contrast, when the determination information of the reliability of the medication administration declaration is transmitted to the terminal MT of the medication administrator or the terminal FT of the family member, the blood pressure measurement value itself may be transmitted together. This allows, for example, the physician to refer to it to, for example, examine the change of the prescription. Alternatively, the medication administration declaration information of the user corresponding to the same determination target period may be transmitted to the terminal MT of the medication administrator or the terminal FT of the family member. At this time, the medication administration ratio may be calculated from the medication administration declaration information, and the calculated medication administration ratio may be transmitted to the terminal MT of the medication administrator or the terminal FT of the family member, together with the declaration information or instead of the declaration information.

Transmitting the declaration information of the medication administration or the medication administration ratio along with the determination result of the reliability of the declaration information as described above allows, for example, the physician and the pharmacist to make more accurate determination in consideration of the reliability of the medication administration declaration notified simultaneously when the medication administration status of the user is determined from the medication administration declaration information.

Further, to notify the medication administration ratio, the medication administration ratio may be corrected (the true medication administration ratio may be predicted) based on the determination result of the reliability of the medication administration declaration. As a method of the correction, for example, it is considered that the medication administration ratio based on the declaration information is reduced at a prescribed percentage (for example, set to 70% of the declaration value).

Further, the determination process of the reliability by the medication administration declaration reliability determination unit 14 can be determined only by a distance from the threshold value according to the declared medication administration ratio, that is, an absolute value of the difference regardless of whether the distance is large or small, as well as the determination whether the degree of dispersion is larger than the threshold value according to the declared medication administration ratio. This makes it possible to determine that the reliability of the declaration is low also in a case where the erroneous declaration "not taken" is made despite that the medicine is actually taken.

Further, for example, when the user forgets administering the medication, the user possibly feels it is a burden to input "not taken" and does not make the declaration itself. For this reason, in a case where there is no declaration by the prescribed percentage or more as described above, in addition to the case it is processed as "no declaration," for example, a case where the declaration has not been made may be regarded that the taking is forgotten (that is, the declaration "not taken" has been made), and the medication administration ratio and the reliability of the declaration may be calculated.

Furthermore, in a case where the medication administration declaration reliability determination unit 14 determines that "a demand to the user for the medication administration declaration is required," the following process is also conceivable. That is, the determination information output unit 15 causes the user terminal UT to display a message prompting the medication administration declaration. The medication administration declaration reliability determination unit 14 determines the presence/absence of a response from the user to the transmission of the message prompting the medication administration declaration, that is, whether the user has performed the input operation of the medication administration declaration information based on the acquisition result of the declaration information by the medication administration declaration information acquisition unit 11. In a case where it is determined that the input operation of the declaration information is not performed, it is regarded that the declaration for the medication administration is not made, and the determination process of the reliability of the declaration information is not performed. In this way, the determination process of the reliability of the declaration information in which the declaration for medication administration is missing can be omitted, which makes it possible to reduce the process load of the user terminal UT.

Actions and Effects

Generally, the degree of dispersion of blood pressure values is associated with the compliance status of the medication administration. For example, seeing the degree of dispersion of blood pressure values measured regularly every day in the target period of one week, the degrees of dispersion of blood pressure values of patients who comply with the medication administration tend to be small, and conversely, the degrees of blood pressure values of patients who do not comply with the medication administration tend to be large.

Thus, in the first embodiment, the medication administration declaration information acquisition unit 11 receives the input of the medication administration declaration information by the user, and concurrently the blood pressure measurement data acquisition unit 12 acquires the blood pressure measurement data of the user from the blood pressure monitor BP and stores it, the dispersion degree calculation unit 13 calculates the degree of dispersion of blood pressure values in the determination target period based on the stored blood pressure measurement data, the medication administration declaration reliability determination unit 14 determines the reliability of the medication administration declaration information declared in the same period based on the degree of dispersion of the blood pressure measurement values, and the determination information output unit 15 transmits the determination result to, for example, the terminal MT of the medication administrator.

Therefore, the medication administrator, such as the physician or the pharmacist, can accurately infer the status of the medication administration of the user as the patient and determine the effect of the medication. In addition, when the determination result of the reliability is transmitted to the terminal FT of, for example, the family member, the family member can directly guide the user himself/herself regarding the declaration for medication administration and confirm whether the medication administration is adequately performed. Further, by displaying the message that demands the declaration for medication administration on the input/display device 3 for the user who tends to forget the declaration for medication administration, a compliance proportion of the medication administration declaration by the user can be increased.

Second Embodiment

In the second embodiment according to the present invention, a subsequent change in the blood pressure is predicted based on the blood pressure measurement data obtained in a past period in which the medication administration status is known, a degree of divergence between the predicted value of the blood pressure and the actually measured value of the blood pressure actually measured is calculated, and reliability of the medication administration declaration information in a medication administration period that affects the blood pressure value in the period in which this degree of divergence is calculated is determined.

For example, based on whether the medication administration ratio is known or the reliability, a period in which the medication administration ratio is corrected is selected as a predicted reference period of blood pressure variation (hereinafter also referred to as a first period). Then, the subsequent blood pressure variation is predicted based on the blood pressure measurement data obtained during the first period, and the degree of divergence between the predicted blood pressure value and the actually measured blood pressure value actually measured in the period of the monitoring target of the blood pressure value (hereinafter also referred to as a second period). Based on the calculated degree of divergence of the blood pressure value, the reliability of the medication administration declaration information of the user in a medication administration period prior to the second period (hereinafter, also referred to as a third period) that affects the blood pressure value (that is, medical efficacy appears) in the second period is determined.

Note that to select the first period, in a case where a period in which the medication administration of the user is accurately managed, such as a period of hospital treatment, is present, this period may be selected as the first period. Furthermore, in a case where a medicine having a quick effect is prescribed or in a case where the user has a physical constitution on which a medicine easily acts, the third period as the determination target period of reliability can be set to be same as the second period, which is the monitoring target period of the degree of divergence.

Further, the first period and the second or third period need not be continuous, and far from it, the periods are preferably not continuous. This is because when the first period is continuous with the second or third period, the degree of change in blood pressure value and the degree of divergence are too small and therefore it is predicted that the comparison cannot be performed.

In addition, in a case where the first period and the second or third period are continuous, ensuring a certain amount of length or more for each period is preferred. This is because this allows reducing an influence from a natural blood pressure variation and an error. In particular, the degree of divergence can be calculated in theory by the use of only the actually measured blood pressure value measured at a certain one timing in the second period. However, to eliminate an influence of the natural blood pressure variation and the error, including a plurality of times of the actually measured blood pressure values is desirable.

Configuration Example

A system in which the medication administration status management device according to the second embodiment is used has a basic configuration same as that of the first embodiment, and thus the description thereof will be omitted. A hardware configuration of the user terminal UT as the medication administration status management device is also the same as that described in the first embodiment, and thus the description thereof will be omitted.
(1) User Terminal UT
(1-1) Software Configuration FIG. 7 is a block diagram illustrating the software configuration of the user terminal UT.

The data storage area in a memory 6 includes a medication administration/blood pressure information storage unit 61 and a prescription information storage unit 62. The medication administration/blood pressure information storage unit 61 stores the input template data used when the user inputs the declaration information of the medication administration. The medication administration/blood pressure information storage unit 61 also stores the declaration information of the medication administration input by the user based on the input template data associated with information representing the date and time of the medication administration. Furthermore, the medication administration/blood pressure information storage unit 61 stores the measurement data of the blood pressure, which is transmitted from the blood pressure monitor BP, associated with information representing the date and time of the measurement. The prescription information storage unit 62 stores prescription information of the target user downloaded from the terminal MT of the medication administrator, such as the physician or the pharmacist, or the EMR server of, for example, a medical institution.

A CPU 5 includes a medication administration declaration information acquisition unit 51, a blood pressure measurement data acquisition unit 52, a blood pressure change prediction unit 53, a blood pressure comparison unit 54, a medication administration declaration reliability determination unit 55, and a determination information output unit 56 as process function units according to the second embodiment. These control units 51 to 56 are all achieved by causing the CPU 5 to execute the application program stored in the program memory area in the memory 6.

The medication administration declaration information acquisition unit 51 is activated by the input request operation of the medication administration declaration by the user, reads the input template data from the medication administration/blood pressure information storage unit 61, and causes the input/display device 3 to display the input template data. Then, the medication administration declaration information acquisition unit 51 performs a process that receives the declaration information of the medication administration input by the user in accordance with the guidance of the input template data from the input/display device 3 and causes the medication administration/blood pressure information storage unit 61 to store the declaration information.

Note that the medication administration declaration information includes, for example, information representing the date and time of the medication administration and information representing the presence or absence of the medication administration on the date and time. For example, in a case where the medication administration timings are designated at, for example, after breakfast, after lunch, after dinner, at wakeup, and at bedtime in the prescription, the information representing the date and time of the medication administration is represented by these pieces of information representing the medication administration timings. The information representing the presence or absence of the medication administration is input for each type of the medicine in the case where there are multiple types of medicines to be administered.

The blood pressure measurement data acquisition unit 52 is activated, for example, by the data transmission request from the blood pressure monitor BP, and performs a process that causes the medication administration/blood pressure information storage unit 61 to store the blood pressure measurement data transmitted from the blood pressure monitor BP and received by the wireless communication circuit 4 together with the information representing the date and time of the measurement. Additionally, at this time, the blood pressure measurement data acquisition unit 52 stores the blood pressure measurement data and the medication administration declaration information such that the blood pressure measurement data and the medication administration declaration information whose date and time of the measurement and date and time of the medication administration correspond to each other are associated.

The blood pressure change prediction unit 53 first selects the past period in which the medication administration status is known as the predicted reference period (the first period) of the blood pressure variation. Then, the blood pressure change prediction unit 53 performs a process that reads the blood pressure measurement data obtained in the first period from the medication administration/blood pressure information storage unit 61 and predicts a subsequent change in the blood pressure value from the blood pressure measurement data.

For example, the blood pressure change prediction unit 53 reads the medication administration declaration information in the first period from the medication administration/blood pressure information storage unit 61, calculates the medication administration ratio based on the medication administration declaration information, and reflects the medication administration ratio to the predicted value of the blood pressure value. In other words, a process of correcting the predicted value of the blood pressure value based on the medication administration ratio during the first period is also performed.

The blood pressure comparison unit 54 sets, for example, the most recent monitoring target period of the blood pressure value (the second period). Then, the blood pressure comparison unit 54 performs a process that reads the blood pressure measurement data (the actually measured value of the blood pressure) obtained in the second period from the medication administration/blood pressure information storage unit 61 and calculates the degree of divergence of the actually measured value of the blood pressure with respect to the predicted value of the blood pressure in the second period obtained by the blood pressure change prediction unit 53.

Based on the degree of divergence of the blood pressure calculated by the blood pressure comparison unit 54, the medication administration declaration reliability determination unit 55 performs a process that determines the reliability of the medication administration declaration information in the medication administration period (the third period), which is prior to the second period, whose medical efficacy appears in the blood pressure value in the second period, for example. An example of the reliability determination will be described later.

The determination information output unit 56 performs a process that generates notification information for notifying the medication administrator, the family member of the user, or the user himself/herself of the determination result of the reliability of the medication administration declaration information by the medication administration declaration reliability determination unit 55, and transmits the notification information to the medication-administrator terminal MT or the terminal FT of the family member, or causes the input/display device 3 to display the notification information.

Operation Example

Next, operations of the user terminal UT configured as described above will be described. FIG. 8 and FIG. 9 are flowcharts exemplifying the operations.
(1) Acquisition of Medication Administration Declaration Information The user terminal UT monitors the operation of the input request for the medication administration declaration information in a standby state in step S20. In this state, assume that the user has performed the tap operation on the icon to which, for example, the medication administration declaration function is assigned in the input/display device 3. Then, the user terminal UT activates the medication administration declaration information acquisition unit 51, and first reads the input template data from the medication administration/blood pressure information storage unit 61 and causes the input/display device 3 to display the input template data in step S21.

In this state, for example, when the user inputs the presence or absence of the medication administration after breakfast, after lunch, and after dinner on the day in accordance with the input template, the input information representing the presence or absence of the medication administration at each meal is received from the input/display device 3 and the medication administration/blood pressure information storage unit 61 is caused to store the information. At this time, information representing date and time at which the medication was administered or date and time at which the medication should be administered (hereinafter collectively referred to as date and time of the medication administration) is given to each piece of the information representing the presence or absence of the medication administration.

For example, some users possibly input the declaration for the medication administration for one day at once after dinner, before going to bed, or the next day or later. In such a case, in a case where the date and time of the input (the date and time of the declaration) is directly regarded as the date and time of the medication administration, the date and time of the declared medication administration differs from the true date and time of the medication administration.

Therefore, for example, as illustrated in FIG. 10 as an example, the input template includes the checkboxes 31a, 32a, and 33a for inputting the presence or absence of the medication administration, and the input fields 31b, 32b, and 33b for the time of the medication administration corresponding to each of after breakfast, after lunch, and after dinner described above about a date and time when the inputs are not performed. Then, the medication administration declaration information storage unit 21 is caused to store the information representing the presence or absence of the medication administration and the information representing the medication administration time input to the corresponding checkboxes 31*a*, 32*a*, and 33*a* and input fields 31*b*, 32*b*, and 33*b* for each of the breakfast, the lunch, and the dinner as the medication administration declaration information.

After that, each time the user performs the input request operation of the medication administration declaration, under the control of the medication administration declaration information acquisition unit 51, the user terminal UT performs a process that receives the above-described medication administration declaration information and causes the medication administration declaration information storage unit 21 to store it.

(2) Acquisition of Blood Pressure Measurement Data

In the standby state, the user terminal UT monitors the transmission request for the blood pressure measurement data from the blood pressure monitor BP in step S52. In this state, when receiving the transmission request for the blood pressure measurement data from the blood pressure monitor BP, the user terminal UT activates the blood pressure measurement data acquisition unit 52, takes in the blood pressure measurement data transmitted from the blood pressure monitor BP and received by the wireless communication circuit 4 from the wireless communication circuit 4, and causes the medication administration/blood pressure information storage unit 61 to store the measurement blood pressure data in step S23. At this time, since the information representing the date and time of the measurement is transmitted along with the blood pressure measurement data, the user terminal UT associates the blood pressure measurement data with the date and time of the measurement, and further associates it with the medication administration declaration information to which the date and time of the medication administration corresponds, and causes the medication administration/blood pressure information storage unit 61 to store it.

Thereafter, each time the user terminal UT receives the transmission request from the blood pressure monitor BP, the user terminal UT performs reception and storage processes of the above-described blood pressure measurement data under the control by the blood pressure measurement data acquisition unit 52.

(3) Prediction of Blood Pressure Change

The user terminal UT monitors a determination request for medication administration declaration reliability while performing the acquisition process of the medication administration declaration information and the acquisition process of the blood pressure measurement data in step S24. In this state, for example, when the user terminal UT receives a determination request from the terminal MT of the medication administrator, such as the physician or the pharmacist, or the terminal FT of the family member, the user terminal UT activates the blood pressure change prediction unit 53.

Under the control by the blood pressure change prediction unit 53, for example, the user terminal UT first selects the past period in which the medication administration status is known as the predicted reference period (the first period) of the blood pressure variation in step S25. Then, the user terminal UT reads the medication administration declaration information and the blood pressure measurement data in the first period (for example, one day or one week) from the medication administration/blood pressure information storage unit 61. Then, the user terminal UT calculates, for example, the medication administration ratio in the medication administration period based on the medication administration declaration information, and predicts the subsequent change in the blood pressure value from the blood pressure measurement data in the medication administration period considering the medication administration ratio. That is, based on the blood pressure value measured in the first period in which the medication administration ratio is known, the change in the blood pressure value in the subsequent period is predicted.

Note that, for example, the blood pressure value is predicted by acquiring guideline data representing the change in the blood pressure value with respect to a dosage for a standard patient from a database, such as the Electronic Medical Records (EMR) server, and referring to the data of this guideline, or using a learning model that learnt the change in the blood pressure based on the past dosage and blood pressure variation history of the user. In addition, in a case where a period in which the medication was surely administered is apparent or a period in which it is apparent that the medication administration ratio is correct due to a reason, such as hospital treatment was performed, is present, this period may be used as the first period described above.

(4) Calculation of Degree of Divergence of Blood Pressure

The user terminal UT subsequently activates the blood pressure comparison unit 54. Under the control by this blood pressure comparison unit 54, the most recent blood pressure monitoring target period (for example, one day, today) is first selected as the second period, and the blood pressure measurement data (the actually measured value of the blood pressure) in the second period is read from the medication administration/blood pressure information storage unit 61 in step S26. Then, among the predicted values of the blood pressure obtained by the blood pressure change prediction unit 53, the degree of divergence (for example, a difference) of the actually measured value of the blood pressure with respect to the predicted blood pressure value obtained in the second period is calculated.

Note that, in the calculation of the degree of divergence, the actually measured value of the blood pressure at a certain time point during the second period may be compared with the predicted value, but the average value of the actually measured blood pressure values measured at a plurality of timings during the second period may be compared with the predicted value. In this way, an influence of temporal blood pressure variations can be reduced.

(5) Determination of Medication Administration Declaration Reliability

When the degree of divergence of the blood pressure value in the second period is calculated, the user terminal UT then activates the medication administration declaration reliability determination unit 55. Then, under the control by the medication administration declaration reliability determination unit 55, in step S27, the medication administration period (for example, yesterday or today) that affects the blood pressure value in the second period, that is, whose medical efficacy appears in the second period is defined as the third period, and the medication administration declaration information in the third period is read from the medication administration/blood pressure information storage unit 61. Then, the read reliability of the medication administration declaration information of the third period read is determined based on the degree of divergence of the blood pressure in the second period calculated by the blood pressure comparison unit 54.

FIG. 9 is a flowchart depicting an example of a procedure and a process content of the determination process of the medication administration declaration reliability. The medication administration declaration reliability determination unit 55 first reads the medication administration declaration information in the third period from the medication administration/blood pressure information storage unit 61 and determines whether any medication administration declaration has been made based on the medication administration declaration information in step S271. In other words, the presence or absence of a missing in the medication administration declaration is determined.

For example, in a case where the third period is one day, insofar as there is at least one medication administration timing at which the medication administration declaration is not made among the medication administration timings designated in the prescription information stored in the prescription information storage unit 62, the medication administration declaration is determined as absent in the day. For example, when the medication administration timing is designated three times, after breakfast, after lunch, and after dinner, and it is declared that taking the medicine is forgotten (no medication administration) after dinner, the medication administration declaration is determined as absent in the day. For example, in a case where the third period is one week, when the number of days in which the medication administration declaration is not made at all is one day or more or the prescribed number of days or more, it is determined that the medication administration declaration is absent in this week. In the case where the medication administration declaration is determined as absent, the medication administration declaration reliability determination unit 55 regards that the medication administration declaration information in the third period is out of the determination target of the medication administration declaration reliability, determines that "a demand to the user for the medication administration declaration is required," and passes the determination result to the determination information output unit 56 in step S272.

On the other hand, when the medication administration declaration is determined as present in the step S271, the medication administration declaration reliability determination unit 55 next determines whether the degree of divergence of the blood pressure value (a difference between the predicted value of the blood pressure and the actually measured value) calculated by the blood pressure comparison unit 54 is greater than or equal to a threshold value in step S273. As a result of the determination, in the case of the degree of divergence of the blood pressure value being greater than or equal to the threshold value, the medication administration declaration reliability determination unit 55 determines that the reliability of the medication administration declaration information in the third period is "low" in step S274. In contrast, in the case of the degree of divergence of the blood pressure value being less than the threshold value, the medication administration declaration reliability determination unit 55 determines that the reliability of the medication administration declaration information in the third period is "high" in step S275.

(6) Output of Determination Result of Medication Administration Declaration Reliability When the medication administration declaration reliability determination unit 55 terminates the determination process of the medication administration declaration reliability, the user terminal UT activates the determination information output unit 56. Then, under the control by the determination information output unit 56, based on the determination result received from the medication administration declaration reliability determination unit 55, a notification message to notify the user himself/herself, the medication administrator, such as the physician and the pharmacist, or the family member of this determination result is generated in step S28.

Then, the notification message for the user himself/herself is output to the input/display device 3 to be displayed, and the notification message for the medication administrator or the family member is output to the wireless communication circuit 4 and transmitted from the wireless communication circuit 4 to the terminal MT of the medication administrator or the terminal FT of the family member.

Note that, in this example, the case in which only the determination information of the reliability of the medication administration declaration is transmitted to the terminal MT of the medication administrator or the terminal FT of the family member has been described. This assumes the case that the medication administration declaration information of the user has been transmitted to the terminal MT of the medication administrator or the terminal FT of the family member by another process. In contrast, when the determination information of the reliability of the medication administration declaration is transmitted to the terminal MT of the medication administrator or the terminal FT of the family member, the medication administration declaration information of the user corresponding to the same medication administration period (the third period) may be transmitted together to the terminal MT of the medication administrator or the terminal FT of the family member FT. At this time, the medication administration ratio may be calculated from the declaration information, and the calculated medication administration ratio may be transmitted to the terminal MT of the medication administrator or the terminal FT of the family member, together with the declaration information or instead of the declaration information.

Transmitting the declaration information of the medication administration or the medication administration ratio along with the determination result of the reliability of the declaration information as described above allows, for example, the physician and the pharmacist to make more accurate determination in consideration of the reliability of the medication administration declaration notified simultaneously when the medication administration status of the user is determined from the medication administration declaration information.

Further, to notify the medication administration ratio, the medication administration ratio may be corrected (the true medication administration ratio may be predicted) based on the determination result of the reliability of the medication administration declaration. As a method of the correction, for example, it is considered that the medication administration ratio based on the declaration information is reduced at a prescribed percentage (for example, set to 70% of the declaration value).

Further, the determination process of the reliability by the medication administration declaration reliability determination unit 55 can be determined only by a distance from the threshold value according to the declared medication administration ratio, that is, an absolute value of the difference regardless of whether the distance is large or small, as well as the determination whether the degree of divergence of the blood pressure is larger than the threshold value according to the declared medication administration ratio. This makes it possible to determine that the reliability of the declaration is low also in a case where the erroneous declaration "not taken" is made despite that the medicine is actually taken.

Further, for example, when the user forgets administering the medication, the user possibly feels burdensome to input "not taken" and does not make the declaration itself. For this reason, in a case where there is no declaration by the prescribed percentage or more as described above, in addition to the case it is processed as "no declaration," for example, a case where the declaration has not been made may be regarded that the taking is forgotten (that is, the declaration "not taken" has been made), and the medication administration ratio and the reliability of the declaration may be calculated.

Furthermore, in a case where the medication administration declaration reliability determination unit 14 determines that "a demand to the user for the medication administration declaration is required," the following process is also conceivable. That is, the determination information output unit 15 causes the user terminal UT to display a message prompting the medication administration declaration. The medication administration declaration reliability determination unit 14 determines the presence/absence of a response from the user to the transmission of the message prompting the medication administration declaration, that is, whether the user has performed the input operation of the medication administration declaration information based on the acquisition result of the declaration information by the medication administration declaration information acquisition unit 11. In a case where it is determined that the input operation of the declaration information is not performed, it is regarded that the declaration for the medication administration is not made, and the determination process of the reliability of the declaration 3o information is not performed. In this way, the determination process of the reliability of the declaration information in which the declaration for medication administration is missing can be omitted, which makes it possible to reduce the process load of the user terminal UT.

Actions and Effects

Generally, the difference between the predicted value and the actually measured value of the blood pressure of the user who complies with the medication administration is considered as small. Therefore, the degree of divergence between the predicted value of the blood pressure in the most recent blood pressure monitoring period (the second period), which is predicted from the blood pressure values measured in the past predicted reference period (the first period) in which the medication administration ratio is known and the actually measured value of the blood pressure value actually measured during the second period tends to be small. In contrast, in a case where the user who does not comply with the medication administration declares for medication administration as if the user complied with the medication administration, it is inferred that the degree of divergence between the predicted blood pressure value and the actually measured value of the blood pressure actually measured actually measured in the second period in which the medical efficacy should appear becomes large.

Thus, in the second embodiment, the blood pressure change prediction unit 53 predicts the change in the blood pressure in the most recent blood pressure monitoring period (the second period) based on the blood pressure measurement data measured in the past predicted reference period (the first period) in which the medication administration ratio is known, and the blood pressure comparison unit 54 calculates the degree of divergence between the predicted value of the blood pressure and the actually measured value of the blood pressure, which was actually measured in the second period. Based on the calculated degree of divergence of the blood pressure, the medication administration declaration reliability determination unit 55 determines the reliability of the medication administration declaration information in the medication administration period (the third period), which is prior to the second period, that affects the blood pressure value (the medical efficacy appears) in the second period, and outputs information representing the determination result to, for example, the terminal MT of the medication administrator by the determination information output unit 56.

Thus, the medication administrator, such as the physician or the pharmacist, can more accurately infer the status of the medication administration during the previous medication administration period that affects the blood pressure in the most recent blood pressure monitoring period of the user as the patient, to determine the effect of the medication. In addition, when the determination result of the reliability of the medication administration declaration is transmitted to the terminal FT of, for example, the family member, the family member can directly guide the user himself/herself regarding the declaration for medication administration and confirm whether the medication administration is adequately performed. Further, by displaying the message that demands the declaration for medication administration on the input/display device 3 for the user who tends to forget the declaration for medication administration, a compliance proportion of the medication administration declaration by the user can be increased.

Modified Examples (1) The reliability of the medication administration declaration determined in the period of the determination target of the medication administration declaration reliability, that is, the target period in the first embodiment or the third period in the second embodiment, may be regarded to be tentatively continued until the reliability of the medication administration declaration is determined next, that is, may be held for a period after the target period or the third period until the present including the second period in the second embodiment. This can be achieved as follows. The medication administration declaration reliability in the target period or the third period determined by the medication administration declaration reliability determination unit 14 or 55 is stored in a reliability storage unit (not illustrated) in the memory 2 until the determination process of the reliability is performed next by the medication administration declaration reliability determination unit 14 or 55, and is updated each time new reliability is obtained.

(2) In the first and second embodiments, the example in which the management function of the medication administration status according to the present invention is provided in the user terminal UT has been described. However, the present invention is not limited thereto. For example, the management function of the medication administration status according to the present invention may be provided in a server device operated by a medical institution, such as a hospital and a pharmacy, or in a server device operated by a service operator related to, for example, a medical treatment, a medicinal drug, or a nursing care.

In such a manner, in a case that the server device is provided with the management function of the medication administration status, for example, the medication administration declaration information input by the user in the user terminal and the biological information measured by the blood pressure monitor can be transmitted from the user terminal to the server device at each fixed period. The server device can receive and store the medication administration declaration information and the biological information transmitted from the user terminal and perform a series of processes described in the first and second embodiments according to the preset determination timing or the input of the determination request from, for example, the physician.

(3) In the first and second embodiments, an example in which the function of the medication administration status management device is provided on the mobile information terminal (the user terminal), such as a smartphone, possessed by the user has been described, However, for example, the function of the medication administration status management device including a blood pressure measurement function may be provided in a wearable terminal.

(4) In the first and second embodiments, the reliability of the medication administration declaration information is determined by comparing the degree of dispersion of the blood pressure value or the degree of divergence of the actually measured value with respect to the predicted value of the blood pressure with one threshold value. However, no such limitation is intended, for example, a plurality of threshold values may be set and the degree of dispersion of the blood pressure value or the degree of divergence of the actually measured value with respect to the predicted value of the blood pressure may be compared with the plurality of threshold values to determine the reliability of the medication administration declaration information in multiple stages.

(5) In the first and second embodiments, the case in which blood pressure measurement data is acquired as the biological information has been described as an example, but measurement data of a blood glucose level, a uric acid level, a creatinine level, a cholesterol level, and a blood oxygen saturation concentration (SPO2) and further measurement data of, for example, a weight, a waist circumference, and a body fat percentage may be acquired, the degree of dispersion or the degree of divergence from the predicted value may be calculated, and the reliability in the medication administration declaration information may be determined based on the result.

(6) In addition, for example, the configuration, the process procedure, and the a process content of the medication administration status management device, the constitution and the notification destination of the information representing the determination result of the reliability of the medication administration declaration information, a selection method and a length of each first, second, and third period described in the second embodiment can be modified and embodied in various ways within a scope not departing from the gist of the present invention.

While the plurality of embodiments and the modified examples according to the present invention have been described in detail above, the above-described description is merely examples of the present invention in all respects, and obviously, various improvements and modifications can be made without departing from the scope of the present invention. That is, specific configurations according to the respective embodiment may be employed as appropriate in the implementation of the present invention.

Additionally, in the present invention, various inventions can be formed by appropriately combining a plurality of components disclosed in the embodiments described above. For example, some components may be omitted from all the components described in the respective embodiments.

Further, the components of the different embodiments may be combined appropriately.

Supplementary Notes

A portion or all of the embodiments can be described as described in the following supplementary notes in addition to the scope of the claims, but is not limited to the supplementary notes.

Supplementary Note 1

A medication administration status management device that includes a hardware processor and a storage medium. The hardware processor is configured to perform: a process that acquires declaration information regarding medication administration of a user; a process that acquires biological information of the user and causes the storage medium to store the biological information; a process that calculates a degree of dispersion of the biological information acquired in a target period based on the biological information stored in the storage medium; a process that determines reliability of the declaration information regarding the medication administration acquired in the target period based on the degree of dispersion of the biological information; and a process that outputs information representing a determination result of the reliability.

Supplementary Note 2

A medication administration status management device that includes a hardware processor and a storage medium. The hardware processor is configured to perform: a process that acquires declaration information regarding medication administration of a user and causes the storage medium to store the declaration information; a process that acquires biological information of the user and causes the storage medium to store the biological information in a state in which the biological information is associable with the declaration information having a corresponding acquisition timing; a process that calculates a predicted value of the biological information in a second period in which the biological information is a monitoring target based on the declaration information and the biological information in a first period in which a medication administration status is known and stored in the storage medium; a process that calculates a degree of divergence of an actually measured value of the biological information acquired during the second period with respect to the calculated predicted value of the biological information; a process that determines reliability of the declaration information regarding the medication administration in a third period that affects a change in the biological information in the second period based on the calculated degree of divergence, the third period being prior to the second period; and a process that outputs information representing a determination result of the reliability.

REFERENCE SIGNS LIST

UT Mobile information terminal
BP Blood pressure monitor
NW Network
MT Medication-administrator terminal
FT Family terminal
1, 5 CPU
2, 6 Memory
3, 100 Input/display device
4, 700 Wireless communication circuit
11, 51, 400 Medication administration declaration information acquisition unit
12, 52, 200 Blood pressure measurement data acquisition unit
13, 300 Dispersion degree calculation unit
14, 55, 500 Medication administration declaration reliability determination unit
15, 56, 600 Determination information output unit
21 Medication administration declaration information storage unit
22 Blood pressure measurement data storage unit
41 Antenna 53 Blood pressure change prediction unit
54 Blood pressure comparison unit
61 Medication administration/blood pressure information storage unit

The invention claimed is:

1. A medication administration status management device comprising:
   a biological information measurement device configured to measure biological information of a user; and
   a processor configured to:
   acquire declaration information regarding medication administration of the user;
   monitor a transmission request from the biological information measurement device to transmit biological information of the user from the biological information measurement device;
   receive from the biological information measurement device the transmitted biological information of the user in response to the transmission request and cause a storage medium to store the biological information that was transmitted in a storage medium;
   calculate a degree of dispersion of the biological information acquired in a target period based on the biological information that was received from the biological information measurement device and stored in the storage medium;
   determine reliability of the declaration information regarding the medication administration acquired in the target period based on the degree of dispersion of the biological information; and
   output information representing a determination result of the reliability, wherein
   the processor determines whether the degree of dispersion of the biological information or a degree of divergence of an actually measured value with respect to a predicted value of the biological information that is calculated is higher than or lower than a threshold value and
   when the processor determines that the degree of dispersion or the degree of divergence of the biological information is higher than the threshold value, the processor generates a message prompting the medication administration or correct declaration for the medication administration, and outputs the message to at least one of a terminal of the user and a terminal of a person involved having a prescribed relationship with the user.

2. The medication administration status management device according to claim 1, wherein
   the processor is further configured to:
   calculate a medication administration ratio representing a ratio of a number of times that the medication is declared to be administered to a total number of declarations for the medication administration in the declaration target period of the medication administration based on the declaration information regarding the medication administration; and
   set the threshold value such that a lower medication administration ratio causes a higher value according to the calculated medication administration ratio.

3. The medication administration status management device according to claim 1, wherein
   the processor is further configured to;
   determine whether there is a missing of a declaration regarding the medication administration in the declaration information based on the declaration information regarding the medication administration; and
   when the missing of the declaration is determined as present, the processor is further configured to determine that the declaration regarding the medication administration needs to be prompted to the user.

4. The medication administration status management device according to claim 3, wherein
   when the processor determines that the declaration regarding the medication administration needs to be prompted to the user, the processor is further configured to output information prompting the declaration regarding the medication administration to the user; and
   the processor is further configured to determine presence or absence of a response from the user to a presentation of the information prompting the declaration regarding the medication administration, and when the response is determined as absent, the processor is further configured to regard that the declaration regarding the medication administration is not made and omit a declaration process of the reliability of the declaration information.

5. The medication administration status management device according to claim 1, wherein the processor is fluffier configured to:
   calculate a medication administration ratio representing a ratio of a number of times that the medication is declared to be administered to a total number of declarations for the medication administration in a declaration target period of the medication administration based on the declaration information regarding the medication administration; and
   correct the medication administration ratio based on a determination result of the reliability of the declaration information.

6. The medication administration status management device according to claim 1, wherein
   the processor is further configured to transmit the information representing the determination result of the reliability to a terminal used by a medication administrator for the user.

7. The medication administration status management device according to claim 1, wherein
   the processor is further configured to cause the storage medium to store the determination result of the reliability, and update the determination result of the reliability stored in the storage medium each time a new reliability determination result is obtained.

8. A non-transitory recording medium that records a program for causing the processor provided with the medication administration status management device according to claim 1 to execute processes in the medication administration status management device.

9. The medication administration status management device according to claim 1, wherein the processor is further configured to acquire the declaration information regarding medication administration of the user by:
   generating a user interface to be displayed on a display device, the user interface including a plurality of input fields configured to receive information relating to the medication administration; and
   receiving information from the user via one or more of the plurality of input fields of the user interface,
   wherein the plurality of input fields are configured to receive information related to a presence or absence of the medication administration and a time of the medication administration.

10. A medication administration status management device comprising:
- a biological information measurement device configured to measure biological information of a user; and
- a processor configured to:
  - acquire declaration information regarding medication administration of the user and cause a storage medium to store the declaration information;
  - monitor a transmission request from the biological information measurement device to transmit biological information of the user from the biological information measurement device,
  - receive from the biological information measurement device the transmitted biological information of the user in response to the transmission request and cause a storage medium to store the biological information that was transmitted in a storage medium in a state in which the biological information is associable with the declaration information having a corresponding acquisition timing;
  - calculate a predicted value of the biological information in a second period in which the biological information is a monitoring target based on the declaration information and the biological information in a first period in which a medication administration status is known and stored in the storage medium;
  - calculate a degree of divergence of an actually measured value of the biological information that was received from the biological information measurement device and acquired during the second period with respect to the calculated predicted value of the biological information;
  - determine reliability of the declaration information regarding the medication administration in a third period that affects a change in the biological information in the second period based on the calculated degree of divergence, the third period being prior to the second period; and
  - output information representing a determination result of the reliability.

11. A non-transitory recording medium that records a program for causing the processor provided with the medication administration status management device according to claim 10 to execute processes in the medication administration status management device.

12. A medication administration status management method performed by an information processing device including a biological information measurement device configured to measure biological information of a user, a processor, and a storage medium, the method comprising:
- acquiring declaration information regarding medication administration of the user and causing the storage medium to store the declaration information by the information processing device;
- monitoring a transmission request from the biological information measurement device to transmit biological information of the user from the biological information measurement device;
- receiving from the biological information measurement device the transmitted biological information of the user in response to the transmission request and causing a storage medium to store the biological information that was transmitted in a storage medium;
- calculating a degree of dispersion of the biological information acquired in a target period based on the biological information that was received from the biological information measurement device and stored in the storage medium;
- determining reliability of the declaration information regarding the medication administration acquired in the target period based on the calculated degree of dispersion of the biological information; and
- outputting information representing a determination result of the reliability, wherein
- the determining the reliability determines whether the degree of dispersion of the biological information or a degree of divergence of an actually measured value with respect to a predicted value of the biological information calculated by the calculating is higher than or lower than a threshold value; and
- when the determining the reliability determines that the degree of dispersion or the degree of divergence of the biological information is higher than the threshold value, the outputting generates a message prompting the medication administration or correct declaration for the medication administration, and the outputting outputs the message to at least one of a terminal of the user and a terminal of a person involved having a prescribed relationship with the user.

13. A medication administration status management method performed by an information processing device including a biological information measurement device configured to measure biological information of a user, a processor and a storage medium, the method comprising:
- acquiring declaration information regarding medication administration of the user and causing the storage medium to store the declaration information by the information processing device;
- monitoring a transmission request from the biological information measurement device to transmit biological information of the user from the biological information measurement device;
- receiving from the biological information measurement device the transmitted biological information of the user in response to the transmission request and causing a storage medium to store the biological information that was transmitted in a storage medium;
- calculating a predicted value of the biological information in a second period in which the biological information is a monitoring target based on the declaration information and the biological information in a first period in which a medication administration status is known and stored in the storage medium by the medication administration status management device;
- calculating a degree of divergence of an actually measured value of the biological information that was received from the biological information measurement device and acquired during the second period with respect to the calculated predicted value of the biological information by the medication administration status management device;
- determining reliability of the declaration information regarding the medication administration in a third period that affects a change in the biological information in the second period based on the calculated degree of divergence by the medication administration status management device, the third period being prior to the second period; and
- outputting information representing a determination result of the reliability by the medication administration status management device.

* * * * *